US005981452A

United States Patent [19]

Schrader et al.

[11] Patent Number: 5,981,452

[45] Date of Patent: Nov. 9, 1999

[54] SYNDET SOAPS COMPRISING ALKYL AND/ OR ALKENYL OLIGOGLYCOSIDES

[75] Inventors: Karlheinz Schrader, Holzminden; Hermann Hensen, Haan; Werner Seipel, Hilden; Mirella Rottmann, Titz, all of Germany

[73] Assignee: Henkel Kommanditgesellschaft auf Aktien, Duesseldorf, Germany

[21] Appl. No.: 08/760,060

[22] Filed: Dec. 4, 1996

Related U.S. Application Data

[60] Provisional application No. 60/023,394, Aug. 13, 1996.

[30] Foreign Application Priority Data

Dec. 4, 1995 [DE] Germany .......................... 195 45 136

[51] Int. Cl.$^{6}$ .............................. A61K 7/50; C11D 17/00

[52] U.S. Cl. .......................... 510/155; 510/151; 510/156; 510/470

[58] Field of Search .................................... 510/141, 155, 510/156, 474, 470, 151, 152

[56] References Cited

U.S. PATENT DOCUMENTS

| | | | |
|---|---|---|---|
| 2,845,391 | 7/1958 | Searle | 510/108 |
| 3,248,333 | 4/1966 | O'Roark | 510/156 |
| 4,100,097 | 7/1978 | O'Roark | 510/156 |
| 4,151,105 | 4/1979 | O'Roark | 510/156 |
| 4,172,887 | 10/1979 | Vanlerberghe et al. | 424/70 |
| 4,234,464 | 11/1980 | Morshauser | 510/141 |
| 4,565,647 | 1/1986 | Llenado | 252/354 |
| 4,606,839 | 8/1986 | Harding | 510/145 |
| 5,043,091 | 8/1991 | Joshi et al. | 510/294 |
| 5,227,086 | 7/1993 | Kacher et al. | 510/146 |
| 5,374,716 | 12/1994 | Biermann et al. | 536/18.6 |
| 5,500,155 | 3/1996 | Weuthen et al. | 510/130 |
| 5,520,840 | 5/1996 | Massaro et al. | 510/151 |
| 5,631,215 | 5/1997 | Kinsman | 510/130 |
| 5,670,471 | 9/1997 | Amalric et al. | 510/416 |

FOREIGN PATENT DOCUMENTS

| | | |
|---|---|---|
| 227 321 | 7/1987 | European Pat. Off. . |
| 30 00 70 | 1/1989 | European Pat. Off. . |
| 301 298 | 2/1989 | European Pat. Off. . |
| 308 189 | 3/1989 | European Pat. Off. . |
| 308 190 | 3/1989 | European Pat. Off. . |
| 463 912 | 1/1992 | European Pat. Off. . |
| 502 616 | 9/1992 | European Pat. Off. . |
| 22 52 840 | 8/1975 | France . |
| 11 65 574 | 3/1964 | Germany . |
| 20 24 051 | 5/1986 | Germany . |
| 40 11 487 | 10/1991 | Germany . |
| 43 31 297 | 3/1995 | Germany . |
| 43 37 031 | 5/1995 | Germany . |
| 43 40 015 | 6/1995 | Germany . |
| WO 90/03977 | 4/1990 | WIPO . |

OTHER PUBLICATIONS

"Surfactants in Consumer Products", Springer Verlag, Berlin, 1987, pp. 54–124 No month available.

"Katalysatoren, Tenside und Mineralöladditive", Thieme Verlag, Stuttgart, 1978, pp. 123–217 No month available.

*Primary Examiner*—Necholus Ogden

*Attorney, Agent, or Firm*—Wayne C. Jaeschke; John E. Drach; Steven J. Trzaska

[57] ABSTRACT

The invention relates to new syndet soaps which contain alkyl and/or alkenyl oligoglycosides as surfactant component and starch as builder. The products are distinguished by a particularly rich and creamy foam and by an optimized feeling on the skin.

4 Claims, No Drawings

SYNDET SOAPS COMPRISING ALKYL AND/OR ALKENYL OLIGOGLYCOSIDES

BENEFIT OF EARLIER FILING DATE UNDER 37 CFR 1.78(a)(4)

This application claims the benefit of earlier filed and copending provisional application Ser. No. 60/023,394, filed on Aug. 13, 1996, the entire contents of which are incorporated herein by reference.

BACKGROUND OF THE INVENTION

1. Field of the Invention

This invention relates to fatty-acid-free syndet soaps containing alkyl and/or alkenyl oligoglycosides and starch.

2. Description of the Related Art

Bar soaps play an important part in personal hygiene. Today, bar soaps are industrially produced by continuous saponification of free fatty acids with alkalis, concentration of the basic soaps and spray drying. A distinction is drawn between true alkali soaps, which contain only fatty acid salts and optionally free fatty acids, and so-called "combination bars", i.e. bar soaps which—in addition to fatty acid salts—contain other synthetic surfactants, generally fatty alcohol ether sulfates or fatty acid isethionates. By contrast, a special position is occupied by so-called "syndet bars" which, apart from impurities, are free from fatty acid salts and contain only synthetic surfactants.

In Germany alone, several million bars of soap for personal hygiene are sold annually. However, the commercial requirements which these mass consumption articles are expected to satisfy are becoming increasingly more stringent. Bar soaps are required not only to clean, but also to care for the skin, i.e. to prevent the skin from drying out, to "ref at" the skin and to protect it against outside influences. The soap is of course expected to be particularly compatible with the skin, but at the same time to produce an abundant and creamy foam in use and to have a pleasant feeling on the skin. In this connection, manufacturers of bar soaps are constantly looking for new ingredients which satisfy these increased requirements.

In recent years, alkyl glucosides have acquired significance as new nonionic surfactants because they behave like anionic surfactants in many respects, for example in their foaming power, and at the same time show extremely high ecological and dermatological compatibility. Accordingly, it was logical to experiment with such surfactants in connection with bar soaps. For example, toilet soaps containing 1 to 20% by weight of alkyl polyglucosides and preferably 55 to 66% by weight of soap as builder are known from European patent application EP-A 0 463 912 (Colgate). Toilet soaps containing mild surfactants, including for example those of the alkyl polyglucoside type, are known from EP-A2 0 227 321, EP-B1 0 308 189 and EP-B1 0 308 190 (Procter & Gamble). Finally DE-A1 43 31 297 and DE-A1 43 37 031 (Henkel) describe fatty-acid-containing combination bars in which small quantities of alkyl polyglucosides are present. However, the bar soaps obtainable in accordance with the teaching of the prior art do not always develop enough foam and, in addition, are unsatisfactory in regard to foam consistency and, in particular, the feeling they have on the skin. In addition, if free fatty acids are used as refatting agents, extremely serious corrosion problems can occur in manufacturing equipment.

Accordingly, the problem addressed by the present invention was to provide bar soaps which would be free from the disadvantages described above. A particular factor to be taken into consideration in this regard was that the new bar soap compositions would also have to lend themselves to production on an industrial scale, i.e. they would be expected, for example, to show adequate, but not excessive moldability and would not have any tendency to form cracks on drying.

DESCRIPTION OF THE INVENTION

The present invention relates to syndet soaps containing
(a) alkyl and/or alkenyl oligoglycosides and
(b) starch.

It has surprisingly been found that bar soaps with improved foaming capacity and an optimized feeling on the skin can be produced in the absence of fatty acids or fatty acid salts providing alkyl and/or alkenyl oligoglycosides, preferably in water-free form, are used as the surfactant component and starch is used as builder. The invention includes the observation that the mixtures are also eminently suitable for the industrial production of bar soaps, i.e. they are stable during storage in air, are substantially non-hygroscopic, are moldable but not too hard and do not crack on drying.

Alkyl and/or alkenyl oligoglycosides

Alkyl and alkenyl oligoglycosides are known nonionic surfactants corresponding to formula (I):

$$R^1O\text{—}[G]_p \qquad (I)$$

in which $R^1$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry. EP-A1 0 301 298 and WO 90/03977 are cited as representative of the extensive literature available on the subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides.

The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred.

In addition, the alkyl or alkenyl radical $R^1$ may also be derived from primary alcohols containing 12 to 22 and preferably 12 to 14 carbon atoms. Typical examples are lauryl alcohol, myristyl alcohol, c yl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ cocoalcohol with a DP of 1 to 3 are preferred.

Starch

It is particularly preferred to use wheat and/or corn starch which may be used in untreated form or preferably in digested, i.e. partly hydrolyzed, form. In one particular embodiment of the invention, compounds of alkyl glucosides and starch are produced by subjecting aqueous slurries of the two components to drying with superheated steam, as described for example in German patent application DE-A1 43 40 015 (Henkel), to which reference is hereby specifically made. However, drying may also be carried out by other processes, for example in a horizontally arranged thin-layer evaporator ("Flash Dryer").

Surfactants

The syndet soaps according to the invention may also contain anionic, nonionic, cationic and/or amphoteric or zwitterionic surfactants as constituents. Typical examples of anionic surfactants are alkylbenzenesulfonates, alkanesulfonates, olefin sulfonates, alkylether sulfonates, glycerol ether sulfonates, $\alpha$-methyl ester sulfonates, sulfofatty acids, alkylsulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl tartrates, acyl glutamates, acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, fatty acid N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Typical examples of cationic surfactants are quaternary ammonium compounds and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines.

The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217. Preferred surfactants are alkyl sulfates, alkyl ether sulfates, sulfosuccinates, ether carboxylic acids, monoglyceride sulfates and/or fatty acid isethionates.

Syndet Soars

Syndet soaps with a particularly favorable feeling on the skin and a creamy foam contain the ingredients in the following quantities:

(a) 5 to 25 and preferably 10 to 20% by weight of alkyl and/or alkenyl oligoglycosides, (b) 5 to 40 and preferably 15 to 30% by weight of starch and (c) 0 to 50 and preferably 25 to 45% by weight of other surfactants, with the proviso that the quantities add up to 100% by weight.

Other preferred constituents of the syndet soaps according to the invention are fatty alcohols and polyethylene glycol ethers. Typical examples of suitable fatty alcohols are lauryl alcohol, myristyl alcohol, cetearyl alcohol, stearyl alcohol and isostearyl alcohol. Suitable polyethylene glycol ethers are those which have an average molecular weight in the range from 5,000 to 20,000 dalton.

COMMERCIAL APPLICATIONS

The syndet soaps according to the invention are substantially free from fatty acids or fatty acid salts, i.e. the content of these substances is below 0.5% by weight. Nevertheless, the soaps produce a surprisingly large amount of a particularly creamy foam in use and, in addition, have a particularly pleasant feeling on the skin.

Auxiliaries and Additives

The syndet soaps may contain oils, emulsifiers, superfatting agents, fats, waxes, stabilizers, cationic polymers, silicone compounds, pigments, biogenic agents, preservatives, dyes and fragrances as further auxiliaries and additives.

Suitable oils are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{6-20}$ fatty alcohols, esters of linear $C_{6-18}$ fatty acids with branched alcohols, more particularly 2-ethyl hexanol, esters of linear and/or branched fatty acids with polyhydric alcohols (for example dimer diol or trimer diol) and/or Guerbet alcohols, triglycerides based on $C_{6-10}$ fatty acids, vegetable oils, branched primary alcohols, substituted cyclohexanes, Guerbet carbonates, dialkyl ethers and/or aliphatic or naphthenic hydrocarbons.

Suitable emulsifiers or co-emulsifiers are nonionic, ampholytic and/or zwitterionic interfacially active compounds which are distinguished by a lipophilic, preferably linear, alkyl or alkenyl group and at least one hydrophilic group. This hydrophilic group may be both an ionic group and a nonionic group.

Nonionic emulsifiers contain a polyol group, a polyalkylene glycol ether group or a combination of polyol and polyglycol ether groups, for example, as the hydrophilic group. Preferred syndet soaps are those containing nonionic surfactants from at least one of the following groups as o/w emulsifiers: (a1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group; (a2) $C_{12/18}$ fatty acid monoesters and diesters of adducts of 1 to 30 moles of ethylene oxide with glycerol; (a3) glycerol monoesters and diesters and sorbitan monoesters and diesters of saturated and unsaturated fatty acids containing 6 to 22 carbon atoms and ethylene oxide adducts thereof and (a4) adducts of 15 to 60 moles of ethylene oxide with castor oil and/or hydrogenated castor oil; (a5) polyol esters and, in particular, polyglycerol esters such as, for example, polyglycerol polyricinoleate or polyglycerol poly-12-hydroxystearate. Mixtures of compounds from several of these classes are also suitable. The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

Suitable w/o emulsifiers are: (b1) adducts of 2 to 15 moles of ethylene oxide with castor oil and/or hydrogenated castor oil; (b2) partial esters based on linear, branched, unsaturated or saturated $C_{12/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose); (b3) trialkyl phosphates; (b4) wool wax alcohols; (b5) polysiloxane/polyalkyl polyether copolymers and corresponding derivatives; (b6) mixed esters of pentaerythritol, fatty acids, citric acid and fatty alcohol according to DE-PS 11 65 574 and (b7) polyalkylene glycols.

Suitable cationic polymers are, for example, cationic cellulose derivatives, cationic starch, copolymers of diallyl ammonium salts and acrylamides, quaternized vinyl pyrrolidone/vinyl imidazole polymers such as, for example, LUVIQUAT® (BASF AG, Ludwigshafen, FRG), condensation products of polyglycols and amines, quaternized collagen polypeptides such as, for example, Lauryldimonium Hydroxypropyl Hydrolyzed Collagen (LAMEQUAT® L, Grünau GmbH) or Lauryldimonium Hydroxypropyl Hydroxylated Wheat Protein (GLUADIN® WQ, Grünau Gmb), polyethyleneimine, cationic silicone polymers such as, for example, Amidomethicone or Dow Corning, Dow Corning Co., USA, copolymers of adipic acid and dimethylaminohydroxypropyl diethylenetriamine (CARTARETINE®, Sandoz AG, CH), polyaminopolyamides as described, for example, in FR-A 2 252 840 and crosslinked water-soluble polymers thereof, cationic chitin derivatives such as, for example, quaternized chitosan, optionally in microcrystalline distribution, cationic guar gum such as, for example, JAGUAR® CBS, JAGUAR® C-17, JAGUAR® C-16 (Celanese) or COSMEDIA GUAR® C 261 (Henkel KGaA) and quaternized ammonium salt polymers such as, for example, MIRAPOL® A-15, MIRAPOL® AD-1, MIRAPOL® AZ-1 of Miranol, USA.

Suitable silicone compounds are, for example, dimethyl polysiloxanes, methylphenyl polysiloxanes, cyclic silicones and amino-, fatty-acid-, alcohol-, polyether-, epoxy-, fluorine- and/or alkyl-modified silicone compounds.

Superfatting agents may be selected from such substances as, for example, polyethoxylated lanolin derivatives, lecithin derivatives, polyol fatty acid esters, monoglycerides and fatty acid alkanolamides, the fatty acid alkanolamides also serving as foam stabilizers. Typical examples of fats are glycerides while suitable waxes are inter alia beeswax, paraffin wax or microwaxes, optionally in combination with hydrophilic waxes, for example cetostearyl alcohol. Metal salts of fatty acids, for example magnesium, aluminum and/or zinc stearate, may be used as stabilizers. Titanium dioxide, for example, is a suitable pigment. In the context of the invention, biogenic agents are, for example, plant extracts and vitamin complexes. Suitable preservatives are, for example, phenoxyethanol, formaldehyde solution, parabens, pentanediol or sorbic acid. The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106.

These dyes are normally used in concentrations of 0.001 to 0.1% by weight, based on the mixture as a whole.

In all, the auxiliaries and additives may make up 1 to 50 and preferably 5 to 40% by weight of the syndet soaps.

EXAMPLES

Bar soaps were molded on the basis of the following formulations F1 (syndet bar, invention) and F2 (combination bar, comparison) and tested for their performance properties. The composition of the bar soaps and the results of the tests are set out in Table 1.

TABLE 1

Compositions (water to 100% by weight) and properties of the bar soaps:

| Component | CTFA Name | F1 % by weight | F2 % by weight |
|---|---|---|---|
| PLANTAREN ® APG 1200 granules | Dodecyl Polyglucose | 15.0 | 15.0 |
| TEXIN ® 128 P | Monolauryl Sulfosuccinate | 40.0 | 40.0 |
| Paraffin (Mp. 54° C.) | | 8.0 | 8.0 |
| HYDRENOL ® DD | Tallow Fatty Alcohol | 17.0 | 17.0 |
| Corn Starch RG 3453 | | 20.0 | — |
| EDENOR ® HK 12–18 | Coco Fatty Acid | — | 20.0 |
| Titanium dioxide | | 1.0 | 1.0 |
| Feeling on the skin | | +++ | + |
| Friction foam | | +++ | + |
| Tendency to absorb water | | − | + |
| Moldability | | +++ | + |
| Crack formation after drying | | − | + |

According to all the test criteria, the Example and Comparison Example show distinct advantages for the syndet bar formulation according to the invention. The syndet bar has a very pleasant feeling on the skin (+++) and generates a large amount of creamy friction foam (+++). It does not have any tendency to absorb water (−) or to crack after drying (−), but at the same time shows excellent moldability (+++). By contrast, the combination bar formulation shows only an average feeling on the skin and foaming power (+), is comparatively difficult to mold (+) and tends both to crack (+) and to absorb water (+).

What is claimed is:

1. A syndet soap bar comprising: (a) from about 5 to about 25% by weight of alkyl and/or alkenyl oligoglycosides, (b) from about 5 to about 40% by weight of starch selected from the group consisting of wheat starch, corn starch, and mixtures thereof and, (c) up to about 50% by weight of an anionic surfactant.

2. The soap bar of claim 1 wherein said anionic surfactant is selected from the group consisting of alkyl sulfates, alkyl ether sulfates, sulfosuccinates, ether carboxylic acids, monoglyceride sulfates, fatty acid isethionates or a combination thereof.

3. The soap bar of claim 1 wherein the content of free fatty acids or fatty acid salts is below about 0.5% by weight.

4. The soap bar of claim 1 further comprising an additional surfactant selected from the group consisting of a cationic surfactant, an amphoteric surfactant, a zwitterionic surfactant and mixtures thereof.

* * * * *